(12) United States Patent
Ali et al.

(10) Patent No.: US 7,223,826 B2
(45) Date of Patent: May 29, 2007

(54) AMIDE-FUNCTIONAL POLYMERS, COMPOSITIONS, AND METHODS

(75) Inventors: Mahfuza B. Ali, Mendota Heights, MN (US); Sumita B. Mitra, West St. Paul, MN (US); Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/626,341

(22) Filed: Jul. 24, 2003

(65) Prior Publication Data
US 2004/0162375 A1 Aug. 19, 2004

Related U.S. Application Data

(60) Provisional application No. 60/444,200, filed on Jan. 30, 2003.

(51) Int. Cl.
*C08F 20/54* (2006.01)
(52) U.S. Cl. .............................. 526/307.5; 526/303.1; 526/307.7; 526/320; 526/328.5; 524/555; 524/556
(58) Field of Classification Search ............. 526/303.1, 526/307.5, 307.7, 320, 328.5; 524/555, 556
See application file for complete search history.

(56) References Cited

U.S. PATENT DOCUMENTS

| | | | |
|---|---|---|---|
| 3,786,116 A | 1/1974 | Milkovich et al. |
| 3,842,059 A | 10/1974 | Milkovich et al. |
| 4,018,732 A | 4/1977 | Lakshmanan |
| 4,071,424 A | 1/1978 | Dart et al. |
| 4,659,572 A | 4/1987 | Murray |
| 4,693,935 A | 9/1987 | Mazurek |
| 4,732,930 A * | 3/1988 | Tanaka et al. ............... 524/742 |
| 4,871,786 A | 10/1989 | Aasen et al. |
| 5,130,347 A | 7/1992 | Mitra |
| 5,152,758 A * | 10/1992 | Kaetsu et al. ............. 604/890.1 |
| 5,154,762 A | 10/1992 | Mitra et al. |
| 5,252,318 A | 10/1993 | Joshi et al. |
| 5,262,055 A * | 11/1993 | Bae et al. ................... 210/645 |
| 5,410,016 A | 4/1995 | Hubbell et al. |
| 5,429,826 A | 7/1995 | Nair et al. |
| 5,468,477 A | 11/1995 | Kumar et al. |
| 5,501,727 A | 3/1996 | Wang et al. |
| 5,545,676 A | 8/1996 | Palazzotto et al. |
| 5,580,929 A | 12/1996 | Tanaka et al. |
| 5,607,663 A | 3/1997 | Rozzi et al. |
| 5,612,052 A | 3/1997 | Shalaby |
| 5,662,887 A | 9/1997 | Rozzi et al. |
| 5,725,882 A | 3/1998 | Kumar et al. |
| 5,866,630 A | 2/1999 | Mitra et al. |
| 5,876,208 A | 3/1999 | Mitra et al. |
| 5,888,491 A | 3/1999 | Mitra et al. |
| 5,922,786 A | 7/1999 | Mitra et al. |
| 5,929,214 A * | 7/1999 | Peters et al. ................ 530/417 |
| 5,939,485 A | 8/1999 | Bromberg et al. |
| 5,942,209 A | 8/1999 | Leavitt et al. |
| 5,976,648 A | 11/1999 | Li et al. |
| 6,018,033 A | 1/2000 | Chen et al. |
| 6,030,634 A | 2/2000 | Wu et al. |
| 6,060,582 A | 5/2000 | Hubbell et al. |
| 6,083,421 A | 7/2000 | Huang et al. |
| 6,121,341 A | 9/2000 | Sawhney et al. |
| 6,123,667 A | 9/2000 | Poff et al. |
| 6,136,885 A | 10/2000 | Rusin et al. |
| 6,162,241 A | 12/2000 | Coury et al. |
| 6,177,095 B1 | 1/2001 | Sawhney et al. |
| 6,201,065 B1 | 3/2001 | Pathak et al. |
| 6,217,894 B1 | 4/2001 | Sawhney et al. |
| 6,312,666 B1 | 11/2001 | Oxman et al. |
| 6,312,667 B1 | 11/2001 | Trom et al. |
| 6,312,668 B2 | 11/2001 | Mitra et al. |
| 6,316,011 B1 | 11/2001 | Ron et al. |
| 6,387,977 B1 | 5/2002 | Sawhney et al. |
| 6,410,645 B1 | 6/2002 | Pathak et al. |
| 6,419,906 B1 | 7/2002 | Xu et al. |
| 6,497,729 B1 | 12/2002 | Moussy et al. |
| 6,538,089 B1 * | 3/2003 | Samra et al. ............. 526/307.4 |
| 6,616,946 B1 * | 9/2003 | Meier et al. ................ 424/489 |
| 2002/0197214 A1 | 12/2002 | Bublewitz et al. |
| 2003/0044455 A1 * | 3/2003 | Kazakov et al. ............ 424/450 |
| 2003/0087986 A1 | 5/2003 | Mitra |

(Continued)

FOREIGN PATENT DOCUMENTS

EP 0 173 567 A2 3/1986

(Continued)

OTHER PUBLICATIONS

Hoffman et al., "Thermally Reversible Hydrogels: II. Delivery and Selective Removal of Substances From Aqueous Solutions," *Journal of Controlled Release*, 4, Elsevier Science Publishers, Amsterdam, pp. 213-222 (1986).

(Continued)

*Primary Examiner*—Helen L. Pezzuto
(74) *Attorney, Agent, or Firm*—Sean J. Edman

(57) ABSTRACT

Amide-functional polymers, and compositions including such polymers, are disclosed. The compositions, which optionally may be hardenable, are useful for treating a surface.

34 Claims, No Drawings

U.S. PATENT DOCUMENTS

| | | |
|---|---|---|
| 2003/0166740 A1 | 9/2003 | Mitra et al. |
| 2003/0195273 A1 | 10/2003 | Mitra et al. |
| 2004/0001892 A1* | 1/2004 | Healy et al. ............ 424/486 |
| 2004/0007051 A1* | 1/2004 | Bashir et al. ............ 73/61.62 |
| 2004/0120901 A1 | 6/2004 | Wu et al. |
| 2004/0122126 A1 | 6/2004 | Wu et al. |

FOREIGN PATENT DOCUMENTS

| | | |
|---|---|---|
| EP | 0363095 | 11/1990 |
| EP | 1 004 293 A2 | 5/2000 |
| EP | 1 004 293 A3 | 5/2000 |
| EP | 1 266 570 A1 | 12/2002 |
| GB | 2 229 443 A | 9/1990 |
| JP | 04-41423 * | 2/1992 |
| JP | 04-041423 * | 2/1992 |
| JP | 3 101 714 | 10/2000 |
| JP | 2000319304 | 11/2000 |
| WO | WO 99/32152 A3 | 7/1990 |
| WO | WO 93/17669 A1 | 9/1993 |
| WO | WO 93/23009 A1 | 11/1993 |
| WO | WO 95/24430 A2 | 9/1995 |
| WO | WO 95/24430 A3 | 9/1995 |
| WO | WO 99/32152 A2 | 7/1999 |
| WO | WO 00/00222 A1 | 1/2000 |
| WO | WO 00/28946 A1 | 5/2000 |
| WO | WO 00/44800 A1 | 8/2000 |
| WO | WO 01/17574 A1 | 3/2001 |
| WO | WO 01/30873 A1 | 5/2001 |
| WO | WO 0176549 | 10/2001 |
| WO | WO 03094877 | 11/2003 |

OTHER PUBLICATIONS

Kawakami et al., "Silicone Macromers for Graft Polymer Synthesis," *Polymer Journal*, vol. 14, No. 11, pp. 913-917 (1982).

Kawakami et al., "Synthesis and Copolymerization of Polysilxoane Macromers," *ACS Polymer Preprints 25* (1), pp. 245-246 (1984).

Kawakami et al., "Synthesis of silicone graft polymers and a study of their surface active properties," *Makromal. Chem.*, 185, pp. 9-18 (1984).

Lee et al., "pH-Thermoreversible Hydrogels. I. Synthesis and Swelling Behaviors of the (N-isopropylacrylamide-*co*- acrylamide-*co*-2-hydroxyethyl methacrylate) Copolymeric Hydrogels," *Journal of Applied Polymer Science*, vol. 71, John Wiley and Sons, Inc., pp. 221-231 (1999).

Lee et al., "Thermoreversible Hydrogels. XII. Effect of the Polymerization Conditions on the Swelling Behavior of the N-Isoproplacrylamide," *Journal of Applied Polymer Science, vol. 78*, John Wiley and Sons, Inc., pp. 1604-1611 (2000).

Lee et al., "Thermoreversible Hydrogels. XIV. Synthesis and Swelling Behavior of the (N-isopropylacrylamide-*co*-2-Hydroxyethyl methacrylate) Copolymeric Hydrogels," *Journal of Applied Polymer Science*, vol. 77, John Wiley and Sons, Inc., pp. 1769-1781 (2000).

Nathoo et al., "Comparative 3-Week Clinical Tooth-Shade Evaluation of a Novel Liquid Whitening Gel Containing 18% Carbamide Peroxide and a Commercially Available Whitening Dentrifrice," *A Supplement to Compendium of Continuing Education in Dentistry*, vol. 23, No. 11 (Suppl. 1), Title page, letter from the editor, and pp. 12-17 (8 pp. total) (Nov. 2002).

Senel et al., "Thermoresponsive Isopropylacrylamide-Vinylpyrrolidone Copolymer by Radiation Polymerization," *Journal of Applied Polymer Science vol. 64*, John Wiley and Sons, Inc., pp. 1775-1784 (1997).

* cited by examiner

US 7,223,826 B2

AMIDE-FUNCTIONAL POLYMERS, COMPOSITIONS, AND METHODS

This application claims the benefit of U.S. Provisional Application No. 60/444,200, filed 30 Jan. 2003.

BACKGROUND

Thermally reversible gel compositions including a thermally responsive viscosity modifier are useful for applications in environments where the temperature is generally higher than the ambient or pre-treatment temperature of the composition. Such compositions can be of low viscosity at ambient temperature, but substantially increase in viscosity or thicken to a thickened, semi-solid, or gel-like composition in the higher temperature environment (e.g., an oral environment). Known thermally reversible compositions include, for example, a poly(oxyalkylene) as a thermally responsive viscosity modifier.

What is needed are non-poly(oxyalkylene)-based polymers that may preferably be useful as thermally responsive viscosity modifiers in thermally responsive compositions.

SUMMARY

In one aspect, the present invention provides a reactive polymer including a non-terminal monomeric unit including a pendant ethylenically unsaturated group and monomeric units derived from N-isopropylacrylamide (e.g., polymerized or copolymerized N-isopropylacrylamide). Preferably the pendant ethylenically unsaturated group includes a (meth)acrylate group.

In another aspect, the present invention provides a reactive polymer including a polymeric backbone having at least three ethylenically unsaturated pendant groups and a plurality of pendant groups of the formula —C(O)NHCH(CH$_3$)$_2$ attached to the backbone. Preferably the pendant ethylenically unsaturated group includes a (meth)acrylate group.

In another aspect, the present invention provides a method of preparing a reactive polymer. The method includes: copolymerizing monomers including N-isopropylacrylamide and a hydroxy-functional (meth)acrylate monomer to form a hydroxy-functional polymer; and reacting the hydroxy-functional polymer with a hydroxy-reactive material selected from the group consisting of a (meth)acrylate-functional isocyanate, a (meth)acrylate-functional epoxide, a vinyl azlactone, and combinations thereof. Optionally, the monomers further include acrylamide.

In another aspect, the present invention provides a method of preparing a reactive polymer. The method includes: copolymerizing monomers including N-isopropylacrylamide and vinyl azlactone to form an azlactone-functional polymer; and reacting the azlactone-functional polymer with a hydroxy-functional (meth)acrylate.

In another aspect, the present invention provides a dental composition suitable for use in the oral environment. The dental composition includes: a polymer including monomeric units derived from N-isopropylacrylamide (e.g., polymerized or copolymerized N-isopropylacrylamide); and a dental additive. Preferably the dental composition is in the form of a dispersion, suspension, emulsion, or solution. Preferably the dental composition is an aqueous composition. Preferably the dental composition is thermally responsive. Optionally the dental composition further includes a polymerizable component.

In another aspect, the present invention provides a composition including: a reactive polymer including a non-terminal monomeric unit including a pendant ethylenically unsaturated group and monomeric units derived from N-isopropylacrylamide (e.g., polymerized or copolymerized N-isopropylacrylamide); and water. Preferably the composition is thermally responsive.

In another aspect, the present invention provides a method of treating an oral surface. The method includes: applying a thermally responsive composition in a low viscosity state at a pre-treatment temperature to the oral surface, the composition including water and a polymer including monomeric units derived from N-isopropylacrylamide (e.g., polymerized or copolymerized N-isopropylacrylamide); and allowing the composition to warm to a treatment temperature and exhibit a thermal response. Optionally, applying the composition includes delivering the composition through an orifice, preferably the orifice of a syringe. Optionally, applying the composition includes painting the composition, brushing the composition, syringing the composition, misting the composition, spraying the composition, applying a substrate having the composition thereon, or combinations thereof.

In another aspect, the present invention provides a method of hardening a composition on a surface. The method includes: applying a thermally responsive composition in a low viscosity state at a pre-treatment temperature to the surface, the composition including water and a reactive thermally responsive viscosity modifier including a polymer including a non-terminal monomeric unit including a pendant ethylenically unsaturated group and monomeric units derived from N-isopropylacrylamide (e.g., polymerized or copolymerized N-isopropylacrylamide); allowing the composition to warm to a treatment temperature and exhibit a thermal response; and inducing the reactive thermally responsive viscosity modifier to react.

In another aspect, the present invention provides a thermally responsive composition including: a polymer including monomeric units derived from N-isopropylacrylamide (e.g., polymerized or copolymerized N-isopropylacrylamide); a polymerizable component different than the polymer; and water.

In another aspect, the present invention provides a method of preparing a hardened composition on a surface. The method includes: applying a thermally responsive composition in a low viscosity state at a pre-treatment temperature to the surface, allowing the composition to warm to a treatment temperature; and inducing the polymerizable component to polymerize. The thermally responsive composition includes: a polymer including monomeric units derived from N-isopropylacrylamide (e.g., polymerized or copolymerized N-isopropylacrylamide); a polymerizable component different than the polymer; and water.

In some embodiments of the present invention, the compositions and methods of the present invention provide hardenable compositions (e.g., hardenable gels). Hardenable compositions can offer advantages over unhardenable compositions (e.g., thermally reversible compositions). Advantages after hardening may include, for example, dimensional stability, thermal stability, improved stability to liquids, improved adhesion, and the potential for sustained release of incorporated additives (e.g., dental additives).

Definitions

As used herein, "thermally responsive" refers to the occurrence of a change in a physical property in response to a change in temperature.

As used herein, "thermally responsive viscosity modifier" means a material that may be incorporated into a composition to provide the composition the capability of substantially changing in viscosity (including a phase change, e.g., a single liquid phase to separate into separate liquid-liquid phases or liquid-solid phases) in response to a change in temperature.

As used herein, a "reactive" thermally responsive viscosity modifier is a thermally responsive viscosity modifier that includes a reactive group.

As used herein, a "reactive" group is a group that can react under selected conditions (e.g., in the presence of free radicals or under condensation reaction conditions) with another reactive group or another component (e.g., a crosslinker or a compound with condensation reaction sites). For example, in a polymer that includes a reactive group, the reactive group can react with another reactive group and/or another component to form crosslinks through dimerization, oligomerization, and/or polymerization reactions.

As used herein, "monomeric unit" refers to a unit in a polymer that is derived from an ethylenically unsaturated monomer. For example, polypropylene includes —$CH_2CH(CH_3)$— monomeric units that are derived from the ethylenically unsaturated monomer propylene, $CH_2$=$CH(CH_3)$.

As used herein, the term "polymer" is used to encompass homopolymers (e.g., polymers derived from a single monomer) and copolymers (e.g., polymers derived from two or more different monomers).

As used herein, "pendant" refers to groups that are attached to the polymer backbone.

As used herein, "hardenable" refers to a material that can be "hardened." As used herein, "harden" is meant to encompass processes including, for example, crosslinking, dimerization, oligomerization, and/or polymerization reactions.

As used herein, "(meth)acryl" is an abbreviation intended to refer collectively to "acryl" and/or "methacryl."

As used herein, "a," "at least one," and "one or more" are used interchangeably.

As used herein, the recitations of numerical ranges by endpoints include all numbers subsumed within that range (e.g., 1 to 5 includes, for example, 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS

In one aspect of the present invention, a dental composition suitable for use in the oral environment is provided. The dental composition includes a polymer including monomeric units derived from N-isopropylacrylamide (e.g., polymerized or copolymerized N-isopropylacrylamide, as described in detail herein below) and a dental additive. The dental composition optionally includes a polymerizable component. Optionally, the composition is thermally responsive. Preferably the composition is in the form of a dispersion, suspension, emulsion, or solution. Preferably the composition is an aqueous composition.

In another aspect of the present invention, a reactive polymer is provided. In one embodiment, the reactive polymer includes a pendant ethylenically unsaturated group and monomeric units derived from N-isopropylacrylamide (e.g., polymerized or copolymerized N-isopropylacrylamide). In another embodiment, the reactive polymer includes a polymeric backbone having at least three ethylenically unsaturated pendant groups and a plurality of pendant groups of the formula —$C(O)NHCH(CH_3)_2$ attached to the backbone. In preferred embodiments, the reactive polymers in combination with water form thermally responsive compositions. Preferably, the thermally responsive compositions are dental compositions suitable for use in the oral environment.

A thermally responsive composition is generally provided in a low viscosity state at a pre-treatment temperature prior to application onto a target site (e.g., a surface of a body), but typically becomes highly viscous (e.g., thick, and controllable) or forms a film or coating (e.g., flexible or rigid) at the target site. Once properly applied to the target site, the composition may optionally be hardened to provide a semi-permanent or permanent composition. These compositions are generally easily dispensed, applied, and manipulated when handled by the user, and are generally easily controlled upon application to the target site. Because the composition typically has a low viscosity (e.g., a free-flowing fluid state) initially at a pre-treatment temperature, it generally requires, for example, lower syringe extrusion forces to deliver the composition to the intended site. In addition, the low viscosity compositions can provide the ability to spray a fine mist or aerosol to a relatively large surface area (e.g., an oral cavity), typically allowing subsequent long term retention upon gellation or phase separation on the warm target site. This can allow the user the freedom to select a dispenser or applicator from an array of systems that are incapable of delivering high viscosity materials. In addition, production of low viscosity compositions may allow for easier processing and greater uniformity and consistency.

Thermally responsive compositions are generally suitable for use in or on living tissues where a composition having a pre-treatment temperature at or lower than ambient (e.g., room temperature) is applied to hard and/or soft tissue that is near or at oral temperature (e.g., 30° C. to 39° C.).

The ability to optionally harden (e.g., with light) a thermally responsive composition in vivo can provide materials that exhibit enhanced physical properties and the advantage of not reverting to a fluid state upon cooling or simple aqueous dilution. Moreover, many of the problems of formulation, handling, delivery, and application of viscous compositions may be overcome, since the compositions of the present invention may be free-flowing liquids prior to treatment.

In a preferred embodiment of the invention, the initial viscosity of the unhardened composition at the pretreatment temperature may be low enough such that the composition is in a liquid state. Subsequently, upon exposure to treatment temperature (e.g., a temperature at or near oral temperature), the viscosity can increase to thicken the composition. A viscosity increase in the range of 5-fold, 10-fold, or even 100-fold or more can be experienced when the initial viscosity is such that the composition is a liquid. Thus, for example, a composition in a liquid state may have a viscosity of 0–7000 poise. In response to an increase in temperature, the viscosity of the composition can increase to at least 10,000 poise. Upon lowering the temperature, the unhardened composition preferably has the ability to reverse its viscosity and return to the flow properties of a liquid. Alternatively, upon increasing the temperature from the pretreatment temperature to the treatment temperature, the thermally responsive composition may separate into phases, resulting, for example, in the formation of a precipitate or a film.

The pre-treatment temperature is the temperature at which the composition is subjected to prior to application or treatment. The pretreatment temperature is preferably at least 5° C. and more preferably at least 20° C. The pretreatment temperature is preferably at most 29° C. and more preferably at most 25° C. However, there may be certain instances where the temperature may be outside this range. A pre-treatment temperature of at least 20° C. allows the composition to be easily stored at ambient or room temperature. A pre-treatment temperature of at most 25° C. allows the composition to be easily stored at ambient or room temperature. However, the compositions of the invention can also be stored at lower, refrigerated pre-treatment temperatures of 5° C. to 10° C. to provide improved stability and shelf life. Preferably a refrigerated pretreatment temperature is at least 5° C. Preferably a refrigerated pretreatment temperature is at most 10° C. The treatment temperature is the temperature at which the composition is exposed to during application. The treatment temperature can be at or near body temperature. Preferably the treatment temperature is at least 30° C. Preferably the treatment temperature is at most 39° C.

Compositions of the present invention optionally include a reactive polymer. The reactive polymer includes a non-terminal monomeric unit including a pendant ethylenically unsaturated group and monomeric units derived from N-isopropylacrylamide (e.g., polymerized or copolymerized N-isopropylacrylamide). Compositions of the present invention preferably include at least 1% by weight of the reactive polymer and more preferably at least 10% by weight of the reactive polymer, based on the total weight of the composition. Compositions of the present invention preferably include at most 99% by weight of the reactive polymer and more preferably at most 90% by weight of the reactive polymer, based on the total weight of the composition.

In some embodiments, compositions of the present invention preferably include at least 30% by weight of water, and more preferably at least 40% by weight of water, based on the total weight of the composition. In some embodiments, compositions of the present invention preferably include at most 90% by weight of water, and more preferably at most 80% by weight of water, based on the total weight of the composition. Water is preferably purified by methods including, for example, distillation, filtration, and ion-exchange processes. In addition to water, compositions of the present invention may optionally include a solvent. Useful solvents include, for example, polyols (e.g., propylene glycol, poly(ethylene glycol), and glycerin). Preferably the solvent is a water miscible solvent.

Compositions of the present invention may be prepared as a single part liquid or gel by combining the above components. For example, the polymer and any additional components may be mixed at the desired temperature (e.g., room temperature). Alternatively, compositions of the present invention may be prepared as multiple part liquids and/or gels that are mixed prior to delivery to the tissue. Such multiple part systems may provide shelf stability that may not exist in single part compositions including, for example, compositions including an initiator system based on two-component redox chemistry, and compositions including an additive that is incompatible with other materials in the composition.

Poly(N-Isopropylacrylamide) Polymers

Polymers that include monomeric units derived from N-isopropylacrylamide (e.g., polymerized or copolymerized N-isopropylacrylamide) can be prepared by any suitable method known to one of skill in the art. Such methods include, for example, those disclosed in the Examples. In brief, polymers that include monomeric units derived from N-isopropylacrylamide can be prepared by homopolymerizing or copolymerizing N-isopropylacrylamide.

Polymers that include monomeric units derived from N-isopropylacrylamide preferably include at least 1 mole %, more preferably at least 50 mole %, and most preferably at least 70 mole % of monomeric units derived from N-isopropylacrylamide, based on the total moles of monomeric units.

Suitable monomers to copolymerize with N-isopropylacrylamide may be selected by one skilled in the art to provide useful polymers. Exemplary monomers that may be used in copolymerizations include, for example, acrylic acid, methacrylic acid, itaconic acid, N-vinyl pyrrolidone, n-butyl acrylate, isobutyl acrylate, lauryl acrylate, octadecyl acrylate, 3-(trimethoxysilyl)propyl methacrylate, macromers (e.g., silicone macromers, fluorocarbon macromers, hydrocarbon macromers), trimethylammoniumethyl methacrylate tetrafluoroborate, dimethylhexadecylammoniumethyl methacrylate bromide, 2-(methyl(nonafluorobutyl)sulfonyl)amino)ethyl acrylate, 2-(methyl(nonafluorobutyl) sulfonyl)amino)ethyl methacrylate, dimethylaminoethyl methacrylate, 2-isocyanatoethyl methacrylate, 2-hydroxyethyl methacrylate, vinyl azlactones (e.g., 4,4-dimethyl-2-vinyl-2-oxazolin-5-one), polyethyleneglycol dimethacrylate, and combinations thereof.

Reactive Polymers

In one embodiment, the present invention provides a reactive polymer including a non-terminal monomeric unit including a pendant ethylenically unsaturated group and monomeric units derived from N-isopropylacrylamide (e.g., polymerized or copolymerized N-isopropylacrylamide). In another embodiment, the present invention provides a polymer including a polymeric backbone having at least three ethylenically unsaturated pendant groups and a plurality of pendant groups of the formula —C(O)NHCH(CH$_3$)$_2$ attached to the backbone. Reactive polymers including an ethylenically unsaturated group can react, for example, in the presence of free radicals to form crosslinks through dimerization, oligomerization, and/or polymerization reactions.

The non-terminal monomeric unit including a pendant ethylenically unsaturated group and/or the plurality of pendant groups of the formula —C(O)NHCH(CH$_3$)$_2$ attached to the backbone may be derived, for example, from (meth) acrylate monomers.

In one illustrative method, the reactive polymer can be prepared by copolymerizing monomers including N-isopropylacrylamide and a hydroxy-functional (meth)acrylate monomer to form a hydroxy-functional copolymer. Methods for copolymerizing such monomers are well known to one of skill in the art. Illustrative conditions for copolymerizing N-isopropylacrylamide are disclosed in the Examples.

The hydroxy-functional copolymer can further be reacted with hydroxy-reactive materials including, for example, (meth)acrylate-functional isocyanates, (meth)acrylate-functional epoxides, vinyl azlactones, and combinations thereof, to provide a (meth)acrylate-functional polymer. For the reaction, preferably, at least 0.01 equivalents of hydroxy-reactive material, more preferably at least 0.1 equivalents of hydroxy-reactive material, and most preferably at least 0.2 equivalents of hydroxy-reactive material, per one equivalent of hydroxy in the hydroxy-functional polymer, is mixed with the hydroxy-functional polymer. For the reaction, preferably, at most 2 equivalents of hydroxy-reactive material, more preferably at most 1 equivalent of hydroxy-reactive material, and most preferably at most 0.8 equivalents of hydroxy-reactive material, per one equivalent of hydroxy in the hydroxy-functional polymer, is mixed with the hydroxy-functional polymer.

Preferred (meth)acrylate-functional isocyanates include, for example, 2-isocyanatoethyl methacrylate. Methods for reacting such compounds are well known to one of skill in the art. Illustrative conditions for reacting a (meth)acrylate-functional isocyante with a hydroxy-functional polymer are disclosed in the Examples.

Preferred (meth)acrylate-functional epoxides include, for example, glycidyl methacrylate. Methods for reacting such compounds are well known to one of skill in the art.

Preferred vinyl azlactones include, for example, 4,4-dimethyl-2-vinyl-2-oxazolin-5-one. Methods for reacting such compounds are well known to one of skill in the art. Illustrative conditions for reacting a vinyl azlactone with a hydroxy-functional polymer are disclosed in the Examples.

In another illustrative method, the reactive polymer can be prepared by copolymerizing monomers including N-isopropylacrylamide and a vinyl azlactone to form an azlactone-functional polymer. Methods for copolymerizing such monomers are well known to one of skill in the art. Illustrative conditions for copolymerizing the monomers are described in the Examples.

The azlactone-functional polymer can further be reacted with a hydroxy-functional (meth)acrylate to provide a (meth)acrylate-functional polymer. For the reaction, preferably, at least 0.01 equivalents of hydroxy-functional (meth)acrylate, more preferably at least 0.1 equivalents of hydroxy-functional (meth)acrylate, and most preferably at least 0.2 equivalents of hydroxy-functional (meth)acrylate, per one equivalent of azlactone in the azlactone-functional polymer, is mixed with the azlactone-functional polymer. For the reaction, preferably, at most 2 equivalents of hydroxy-functional (meth)acrylate, more preferably at most 1 equivalent of hydroxy-functional (meth)acrylate, and most preferably at most 0.8 equivalents of hydroxy-functional (meth)acrylate, per one equivalent of azlactone in the azlactone-functional polymer, is mixed with the azlactone-functional polymer.

Preferred hydroxy-functional (meth)acrylates include, for example, 2-hydroxyethyl methacrylate. Methods for reacting such compounds are well known to one of skill in the art. Illustrative conditions for reacting a hydroxy-functional (meth)acrylate with an azlactone-functional polymer are disclosed in the Examples.

Reactive polymers preferably include at least 1 mole %, more preferably at least 50 mole %, and most preferably at least 70 mole % of monomeric units derived from N-isopropylacrylamide, based on the total moles of monomeric units. Reactive polymers preferably include at most 99 mole %, more preferably at most 95 mole %, and most preferably at most 90 mole % of monomeric units derived from N-isopropylacrylamide, based on the total moles of monomeric units.

Reactive polymers preferably include at least 1 mole %, more preferably at least 5 mole %, and most preferably at least 10 mole % of non-terminal monomeric units comprising a pendant ethylenically unsaturated group, based on the total moles of monomeric units. Reactive polymers preferably include at most 90 mole %, more preferably at most 50 mole %, and most preferably at most 30 mole % of non-terminal monomeric units comprising a pendant ethylenically unsaturated group, based on the total moles of monomeric units.

Other monomers that may be used in the copolymerization include, for example, those disclosed in the Examples.

Initiator System

Compositions of the present invention that include a reactive polymer and/or a polymerizable component preferably also include an initiator system (e.g., one or more initiators) or catalyst that enables the composition to be hardened. For example, visible and/or near-infrared photoinitiator systems may be used to initiate photopolymerization in compositions including free-radically polymerizable components. For example, a monomer can be combined with a three component or ternary photoinitiator system including a sensitizer, an electron donor, and an iodonium salt as disclosed, for example, in U.S. Pat. No. 5,545,676 (Palazzotto et al.). Alternatively, the composition may include a binary initiator system including a sensitizer (e.g., camphorquinone) and an electron donor (e.g., a secondary or a tertiary alkyl amine compound as disclosed, for example, in U.S. Pat. No. 4,071,424 (Dart et al.)).

Another class of useful photoinitiators includes acylphosphine oxides, as disclosed in European Pat. Publ. No. 173,567 (Ying). Such acylphosphine oxides are of the general formula $(R)_2 P(=O)C(=O)-R^1$, wherein each R individually can be a hydrocarbyl group (e.g., alkyl, cycloalkyl, aryl, and aralkyl), which may be substituted with a halo-, alkyl- or alkoxy-group, or the two R groups may be joined to form a ring along with the phosphorous atom, and wherein $R^1$ is a hydrocarbyl group, an S-, O-, or N-containing five- or six-membered heterocyclic group, or a -Z-C(=O)—P(=O)—$(R)_2$ group, wherein Z represents a divalent hydrocarbyl group (e.g., alkylene or phenylene) having from 2 to 6 carbon atoms.

Preferred acylphosphine oxides useful in the invention are those in which the R and $R^1$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide available under the trade designation IRGACURE 819 from Ciba Specialty Chemicals (Tarrytown, N.Y.).

The use of redox catalysts including oxidants and reductants for inducing free radical polymerization in multi-component systems is also useful for generating hardened gels. A preferred mode of initiating the polymerization reaction uses oxidizing and reducing agents as a redox catalyst system. Various redox systems optionally including microencapsulated reducing and/or oxidizing agents are disclosed in U.S. Pat. No. 5,154,762 (Mitra et al.).

Preferably, the oxidizing agent reacts with or otherwise cooperates with the reducing agent to produce free radicals. The free radicals are capable of initiating polymerization of the ethylenically unsaturated moiety. The oxidizing and reducing agents preferably are sufficiently soluble and are present in an amount sufficient to permit an adequate free radical reaction rate as disclosed in U.S. Pat. No. 6,136,885 (Rusin et al.).

A preferred class of oxidizing agents includes persulfates (e.g., sodium, potassium, ammonium, and alkyl ammonium persulfates). Another preferred class of oxidizing agents includes peroxides or peroxide salts (e.g., hydrogen peroxide, benzoyl peroxide, and hydroperoxides including, for example cumene hydroperoxide, tert-butyl hydroperoxide, tert-amyl hydroperoxide, and 2,5-dihydroperoxy-2,5-dimethylhexane). Other preferred oxidizing agents include salts of cobalt(III) and iron(III), perboric acid and its salts, and salts of a permanganate anion. Combinations of any of the above mentioned oxidizing agents can also be used.

Preferred reducing agents include, for example, amines (e.g., aromatic amines), ascorbic acid, metal complexed ascorbic acid, cobalt(II) chloride, ferrous chloride, ferrous sulfate, hydrazine, hydroxylamine, oxalic acid, thiourea, and salts of dithionite, thiosulfate, benzene sulfinate, or sulfite anions.

If initiators are included in compositions of the present invention, the compositions preferably include at least 0.01% by weight of the initiator and more preferably at least 0.1% by weight of the initiator, based on the total weight of the composition. If initiators are included in compositions of the present invention, the compositions preferably include at most 10% by weight of the initiator and more preferably at most 5% by weight of the initiator, based on the total weight of the composition.

Secondary Polymerizable Component

Compositions of the present invention may optionally include a polymerizable component different than the reactive polymer (e.g., a secondary polymerizable component). If a polymerizable component different than the reactive polymer is included, the composition preferably includes at least 1% by weight of the polymerizable component and more preferably at least 5% by weight of the polymerizable component, based on the total weight of the composition. If a polymerizable component different than the reactive polymer is included, the composition preferably includes at most 90% by weight of the polymerizable component and more preferably at most 80% by weight of the polymerizable component, based on the total weight of the composition.

In certain embodiments, the compositions are photopolymerizable, i.e., the compositions include a polymerizable component and a photoinitiator (i.e., a photoinitiator system) that upon irradiation with actinic radiation initiates the polymerization (or hardening) of the composition. Such photopolymerizable compositions are preferably free radically polymerizable.

In certain embodiments, the compositions are chemically polymerizable, i.e., the compositions contain a chemical initiator system that can polymerize, cure, or otherwise harden the composition without dependence on irradiation with actinic radiation. Such chemically polymerizable compositions are sometimes referred to as "self-cure" compositions and may include, for example, glass ionomer cements (e.g., conventional and resin-modified glass ionomer cements), redox cure systems, silane moieties capable of undergoing a condensation reaction (as described, for example, in U.S. Pat. No. 5,607,663 (Rozzi et al.), U.S. Pat. No. 5,662,887 (Rozzi et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.)), and combinations thereof.

Ethylenically Unsaturated Compounds. Ethylenically unsaturated compounds include, for example, polymerizable monomers, polymerizable oligomers, polymerizable polymers, and combinations thereof. Preferably, the polymerizable component is free radically polymerizable. Preferred monomers, oligomers, and polymers are those which are partially or fully water miscible.

Suitable polymerizable monomers and oligomers include, for example, poly(ethyleneglycol) dimethacrylate (PEGDMA), tetrahydrofurfural methacrylate, as well as hydroxylic functional monomers including, for example, 2-hydroxyethyl methacrylate (HEMA), glycidyl dimethacrylate (GDMA), and glycidyl monomethacrylate (GMMA). Hydrophobic monomers and oligomers including, for example, bis(glycidyl methacrylate) (bis-GMA), tri(ethyleneglycol)dimethacrylate (TEGDMA), and urethane dimethacrylate may also be utilized.

Suitable polymerizable polymers include, for example, partially or fully acrylate- or methacrylate-functionalized polymers including, for example, functionalized poly (acrylic acid) polymers, cellulosics, poly(vinylalcohol) polymers, poly(oxyethylene)-poly(oxypropylene) block copolymers, poly(ethyleneglycol) polymers, and the like.

Chemically Polymerizable Compositions. Chemically polymerizable compositions may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass. The glass ionomer cements may also include resin-modified glass ionomer ("RMGI") cements. Exemplary chemically polymerizable compositions are described, for example, in Applicants' Assignees' copending application Ser. No. 10/327,411, filed Dec. 20, 2002.

The chemically polymerizable compositions may include redox cure systems that include a polymerizable component (e.g., an ethylenically unsaturated polymerizable component) and redox agents. The redox agents may include an oxidizing agent and a reducing agent. Suitable polymerizable components, redox agents, optional acid-functional components, and optional fillers that are useful in the present invention are described in Applicants' Assignees' copending application Ser. Nos. 10/121,326 (published as U.S. 2003-0166740 A1) and 10/121,329 (published as U.S. 2003-0195273 A1), both filed Apr. 12, 2002. Alternatively, the redox agents may include a free-radical initiator system containing enzymes as disclosed in Applicants' Assignees' copending application Ser. No. 10/327,202, filed Dec. 20, 2002.

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently compatible with the composition (and preferably water-miscible) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt(III) chloride and ferric chloride, cerium(IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in Applicants' Assignees' copending application Ser. No. 10/121,329 (published as U.S. 2003-0195273 A1), filed Apr. 12, 2002.

The reducing and oxidizing agents are present in amounts sufficient to permit an adequate free-radical reaction rate. This can be evaluated by combining all of the ingredients of the polymerizable composition except for any optional filler, and observing whether or not a hardened mass is obtained.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-immiscible encapsulant, the reducing and oxidizing agents can be combined with an FAS glass and water and maintained in a storage-stable state.

A redox cure system can be combined with other cure systems, e.g., with a glass ionomer cement and with a photopolymerizable composition such as described U.S. Pat. No. 5,154,762 (Mitra et al.).

The hardenable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

Additives

In some embodiments, compositions of the present invention include, or may optionally include, additives (e.g., medical additives for medical compositions that are suitable for use in or on the body, dental additives for dental compositions that are suitable for use in the oral environment). Exemplary additives include, for example, fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, medicaments, indicators, dyes, pigments, wetting agents, surfactants, buffering agents, viscosity modifiers, thixotropes, fillers, polyols, antimicrobial agents, antifungal agents, stabilizers, agents for treating xerostomia, desensitizers, and combinations thereof. Preferably the additives are dental additives suitable for use in the oral environment.

Useful additives may be selected for specific applications as desired. For example, dental whitening compositions generally include a whitening agent. The whitening agent used in the present invention may be any material that has the effect of whitening teeth. Useful whitening agents include, for example, hypochlorites (e.g., sodium hypochlorite), peroxides, hydroperoxides, hydrogen peroxide, peracids (also known as peroxyacids), carbamide peroxide (i.e., the urea complex of hydrogen peroxide, $CO(NH_2)_2H_2O_2$, also known as urea hydrogen peroxide, hydrogen peroxide carbamide, or perhydrol-urea), and combinations thereof. The concentration of a whitening agent in the composition can vary depending upon its activity. Compositions of the present invention may be adjusted as desired to include the amount of additive as desired for the specific application.

Compositions of the present invention may also include non-polymerizable polymers. Preferably, the non-polymerizable polymers are partially or fully miscible in an aqueous environment and include, for example, poly(acrylic acid) polymers, cellulosics, poly(vinylalcohol) polymers, poly (oxyethylene)-poly(oxypropylene) block copolymers, poly (ethyleneglycol) polymers, and combinations thereof.

Methods

Methods of the present invention provide for the treatment of a surface.

In one embodiment, the treated surface is the surface (e.g., soft or hard tissue) of a body (e.g., animal or human). Hard tissues include, for example, bone, teeth, and the component parts of teeth (e.g., enamel, dentin, and cementum). Soft tissues include, for example, mucosa (e.g., tongue, gingiva, and throat).

Alternatively, the treated surface may be, for example, a substrate (e.g., a flexible film). Preferably the surface-treated substrate may be shaped or deformed. More preferably, the surface-treated substrate may be shaped or deformed by pressure from the surface of a body (e.g., a hand, a foot, a tooth). If only one surface of the substrate is treated, the pressure may be applied from either side of the substrate.

Compositions of the present invention may be delivered to the desired site by any method as desired. For example, the composition may be delivered directly onto the target site from a container or dispenser. Suitable containers or dispensers include, for example, bottles, vials, syringes, and tubes. The ability to delivery the composition as a bulk liquid from a needle tip or as a fine mist from an aerosol provides versatility in application. Alternatively, the composition can be delivered by using a brush, sponge, applicator, or swab to paint or coat the composition onto the target site. For some applications it may be desirable to apply the composition to larger areas. For those particular applications, the compositions may be delivered via spray or aerosol dispensers or by simply rinsing the entire target area (e.g., the oral cavity) with the liquid. Another alternative mode of delivery includes the use of a tray type dispenser.

Alternatively, the composition can be applied to a substrate, and the substrate having the composition thereon can be applied to the desired surface. Suitable substrates include, for example, polymeric films, paper, and woven and nonwoven sheets. The composition can also be applied to a brush, spatula, medical/dental instrument, or an applicator prior to application to the desired surface.

When the thermally responsive compositions of the present invention include two or more parts, the two or more parts are preferably mixed just prior to or during the application process. Suitable mixing devices include, for example, static mixing devices.

The composition is preferably allowed to stand on the surface of the target site long enough to provide the desired effect. The standing time will vary depending on the particular composition employed, the type of target site (e.g., tissue), the intended use, and the time available for carrying out the procedure. For many applications, the composition may be allowed to remain on the target site for an extended period of time.

Prior to hardening, thermally reversible compositions of the present invention can be readily removed from the target site by cooling the material below the liquid to semi-solid transition temperature, thus reversing the thickening effect. This can be accomplished with cool water or other physiologically compatible liquids. Alternatively, the concentrations of the components in the composition may be adjusted and diluted by adding water or other liquids. By adjusting the concentrations of the components, the transition temperature is correspondingly adjusted, and thus provides the user the ability to remove the composition even with warm solutions. Water or other liquids may be administered through a rinsing cup, squirt bottle, a liquid dispensing dental tool, or any other liquid dispensing device that can provide a liquid to the oral environment. Preferably, administering cool or cold water provides a significant decrease in viscosity. Alternatively, the composition may be brushed, wiped, or blown off.

Compositions of the present invention that include a reactive polymer may be hardened by inducing the reactive polymer to react. If the composition includes an optional polymerizable component different than the reactive polymer, hardening of the composition may also include polymerization of the polymerizable component. For example, when the reactive polymer or the polymerizable component includes an ethylenically unsaturated group, polymerization may be induced by the application of actinic radiation. Preferably the composition is irradiated with radiation having a wavelength of 400 to 1200 nanometers, and more preferably with visible radiation. Visible light sources include, for example, the sun, lasers, metal vapor (e.g., sodium and mercury) lamps, incandescent lamps, halogen lamps, mercury arc lamps, fluorescent room light, flashlights, light emitting diodes, tungsten halogen lamps, and xenon flash lamps.

Alternatively, when the reactive polymer or the polymerizable component includes an ethylenically unsaturated group, the composition may include two or more parts, with one part including an oxidizing agent, and another part including a reducing agent.

Upon exposure to treatment temperature (e.g., a temperature at or near oral temperature) and hardening, the viscosity of the composition can increase to thicken the composition. A viscosity increase in the range of 10-fold, 50-fold, or even 100-fold or more can be experienced when the initial viscosity is such that the composition is a liquid. Alternatively, exposure to treatment temperature (e.g., a temperature at or near oral temperature) and hardening, the thermally responsive composition may separate into phases, resulting, for example, in the formation of a precipitate or a film. Typically, the film or precipitate is insoluble.

Once a composition of the present invention has been hardened, the composition is rendered thermally irreversible and is generally not readily removed by reducing temperature or diluting with water. However, the hardened composition can generally be removed by mechanical or chemical methods including, for example, brushing, wiping, scraping, and use of solvents (e.g., alcohols).

For some embodiments of the present invention, the substantial moisture content of the composition provides the ability to easily deliver or apply, for example, a gel-on-contact aqueous material that provides substantial hydration of tissues that are subject to dehydration. Compositions of the present invention may also be useful for applications including, for example, tissue adhesives and sealants for surgical and medical applications; treatment of periodontal disease; caries reduction gels; oral coatings (with/without local anesthetics) for hard and soft tissues; and dermal and sub-dermal delivery of drugs.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

| Abbreviations/Definitions | |
|---|---|
| NIPAAM | N-Isopropyl acrylamide (Sigma-Aldrich, St. Louis, MO) |
| IEM | 2-Isocyanatoethyl methacrylate (Sigma-Aldrich) |
| AA | Acrylic acid (Sigma-Aldrich) |
| MAA | Methacrylic acid (Sigma-Aldrich) |
| ITA | Itaconic acid (Sigma-Aldrich) |
| NVP | N-Vinyl Pyrrolidone (Sigma-Aldrich) |
| LA | Lauryl acrylate (Sigma-Aldrich) |
| ODA | Octadecyl acrylate (Sigma-Aldrich) |
| A-174 | 3-(Trimethoxysilyl)propyl methacrylate (Sigma-Aldrich) |
| SiMac | Silicone macromer of MW approximately 10,000 (prepared as described for making "monomer C 3b" at column 16 of U.S. Pat. No. 4,693,935 (Mazurek)) |
| TMA-BF$_4$ | Trimethylammoniumethyl methacrylate tetrafluoroborate (Prepared as described for SM-1) |
| DMA-C$_{16}$Br | Dimethylhexadecylammoniumethyl methacrylate bromide (Prepared as described for SM-2) |
| MeFBSEA | 2-(Methyl(nonafluorobutyl)sulfonyl)amino)ethyl acrylate (Prepared as described in Example 2 of International Publication No. WO 01/30873 (Savu et al.)) |
| MeFBSEMA | 2-(Methyl(nonafluorobutyl)sulfonyl)amino)ethyl methacrylate (Prepared as described in Example 2 of International Publication No. WO 01/30873 (Savu et al.)) |
| DMAEMA | Dimethylaminoethyl methacrylate (Sigma-Aldrich) |
| HEMA | 2-Hydroxyethyl methacrylate (Sigma-Aldrich) |
| AAM | Acrylamide (Sigma-Aldrich) |
| IBMA | Isobutyl methacrylate (Sigma-Aldrich) |
| VDMA | Vinyl dimethyl azlactone (4,4-dimethyl-2-vinyl-2-oxazolin-5-one; Group SNPE, Strasbourg, France) |
| PEGDMA 400 | Polyethyleneglycol dimethacrylate (Sartomer, Exton, PA) |
| VAZO-67 | 2,2'-Azobis(2-methylbutanenitrile) (Dupont, Wilmington, DE) |
| V-50 | 2,2'-Azobis(2-amidinopropane) dihydrochloride (WAKO, Richmond, VA) |
| DBTDL | Dibutyltin dilaurate (Sigma-Aldrich) |
| DBU | 1,8-Diazabicyclo(5.4.0)undec-7-ene (Sigma-Aldrich) |
| CPQ | Camphorquinone (Sigma-Aldrich) |
| EDMAB | Ethyl 4-(N,N-dimethylamino)benzoate (Sigma-Aldrich) |

-continued

| Abbreviations/Definitions | |
|---|---|
| DPIHFP | Diphenyliodonium hexafluorophosphate (Johnson Matthey, Alpha Aesar Division, Ward Hill, NJ) |
| BHT | 2,6-Di-tert-butyl-4-methylphenol (Sigma-Aldrich) |
| THF | Tetrahydrofuran (Sigma-Aldrich) |
| DMF | Dimethyl formamide (Sigma-Aldrich) |

PREPARATION OF STARTING MATERIALS

Polymer A: Preparation of Poly(NIPAAM(76)/HEMA(16)/AAM(8))

NIPAAM (10 parts), HEMA (1.0 parts), AAM (1.0 parts), VAZO-67 (0.22 parts), and THF (25 parts) were combined in a reaction bottle and the resulting mixture purged with nitrogen for 2 minutes. The bottle was sealed and maintained at 60° C. in a constant temperature rotating device for 17 hours. The resulting viscous polymer solution was poured into a large excess (approximately 5 times volume of reaction mixture) of cyclohexane and the precipitated solid collected by filtration and dried in a 30° C. vacuum oven. The dried powdery solid was designated Polymer A and identified as the polymer of NIPAAM (76), HEMA (16), and AAM (8) with weight ratios indicated in parentheses.

Polymers B–E: Preparation of NIPAAM-Derived Polymers

Polymers B–E were prepared as described for Polymer A and are listed as follows with monomeric units and weight ratios indicated:
Polymer B: NIPAAM(93.3)/AAM(6.5)
Polymer C: NIPAAM(76.9)/AAM(7.7)/VDMA(15.4)
Polymer D: NIPAAM(83.3)/HEMA(16.7)
Polymer E: NIPAAM(76.9)/VDMA(23.1)

Polymers F and G: Preparation of NIPAAM-Derived Polymers

Polymers F and G were prepared as described for Polymer A, except that 3-mercaptopropionic acid (Sigma-Aldrich) was used as a chain transfer agent (0.62 parts), tert-butanol was used as a solvent, and the polymer was precipitated in hexane. Polymers F and G and are listed as follows with monomeric units and weight ratios indicated:
Polymer F: $HO_2CCH_2CH_2CH_2S$-(NIPAAM(71.5)/HEMA (28.5))
Polymer G: $HO_2CCH_2CH_2CH_2S$-(NIPAAM(76.9)/HEMA (15.5)/AAM (7.6))

Starting Material 1 (SM-1): Synthesis of Trimethylammoniumethyl Methacrylate Tetrafluoroborate (TMA-$BF_4$)

A three-necked flask fitted with a mechanical stirrer, a dropping funnel and a condenser was charged with 80 parts of sodium tetrafluoroborate (Alfa Aesar Inorganics, Ward Hill, Mass.) and 130 parts of DI water. The mixture was stirred for 15 minutes and a clear solution was obtained. From the dropping funnel a solution of 202.4 parts of dimethylaminoethyl methacrylate-methyl chloride (trimethylammoniumethyl methacrylate chloride; CPS Company, Ciba, Crystal Lake, Ill.) and 80 parts of DI water was added slowly. A solid product immediately began to precipitate out. After the addition was complete, the mixture was stirred for 30 minutes and the solid isolated by filtration, washed with 30 parts of DI water, and dried under vacuum at 40° C. An NMR analysis of the solid product revealed the structure to be pure trimethylammoniumethyl methacrylate tetrafluoroborate.

Starting Material 2 (SM-2): Synthesis of Dimethylhexadecylammoniumethyl Methacrylate Bromide (DMA-$C_{16}$Br)

A 500-ml round-bottom flask was charged with 42.2 parts of DMAEMA, 154.7 parts of acetone, 93.2 parts of 1-bromohexadecane (Sigma-Aldrich), and 0.34 parts of BHT. The mixture was stirred for 16 hours at 35° C. and then allowed to cool to room temperature. The resulting white solid precipitate was isolated by filtration, washed with cold ethyl acetate, and dried under vacuum at 40° C. An NMR analysis of the solid product revealed the structure to be pure dimethylhexadecylammoniumethyl methacrylate bromide.

Example 1

Derivatization of Polymer C
(NIPAAM/AAM/VDMA) with HEMA

A three-neck reaction flask fitted with a mechanical stirrer, condenser, dropping funnel, and thermometer was charged with 76 parts of a 34.2% THF solution of Polymer C followed by 0.22 parts of 1,8-diazabicyclo(5.4.0)undec-7-ene (Sigma-Aldrich). A solution of HEMA (3.74 parts) in THY (13 parts) was slowly added from the dropping funnel and the resulting solution heated at 40° C. for 30 minutes. The resulting polymer solution was poured into a large excess of cyclohexane (approximately 5 times volume of reaction mixture) and the precipitated solid collected by filtration and dried in a 30° C. vacuum oven. The dried white solid was designated Example 1 and identified as the polymer of NIPAAM/AAM/VDMA with a plurality of the dimethyl azlactone monomeric units derivatized with HEMA to provide monomeric units of the following structure ($Me=CH_3$):
$CH_2=C(Me)CO_2CH_2CH_2OC(O)C(Me)_2NHC(O)$-Polymer backbone.

Example 2

Derivatization of Polymer D (NIPAAM/HEMA) with IEM

A three-neck reaction flask fitted with a mechanical stirrer, condenser, dropping funnel, and thermometer was charged with 76 parts of a 32.4% THF solution of Polymer D followed by (0.25 parts) of dibutyltin dilaurate (Sigma-Aldrich) and 0.01 parts of BHT. A solution of IEM (4.77 parts) in THF (10 parts) was slowly added from the dropping funnel and the resulting solution heated at 40° C. for 30 minutes. The resulting polymer solution was cooled to room temperature, poured into a large excess of cyclohexane (approximately 5 times volume of reaction mixture), and the precipitated solid collected by filtration and dried in a 30° C. vacuum oven. The dried white solid was designated Example 2 and identified as the polymer of NIPAAM/HEMA with a plurality of the HEMA monomeric units derivatized with IEM to provide monomeric units of the following structure ($Me=CH_3$):
$CH_2=C(Me)CO_2CH_2CH_2NHC(O)OCH_2CH_2OC(O)$-Polymer backbone.

Example 3

Derivatization of Polymer E (NIPAAM/VDMA) with HEMA

A three-neck reaction flask fitted with a mechanical stirrer, condenser, dropping funnel, and thermometer was charged with 76 parts of a 34.2% THF solution of Polymer E followed by 0.22 parts of 1,8-diazabicyclo(5.4.0)undec-7-ene and 0.01 parts of BHT. A solution of HEMA (5.61 parts) in THF (5 parts) was slowly added from the dropping funnel and the resulting solution heated at 40° C. for 30 minutes. The resulting polymer solution was cooled to room temperature, poured into a large excess of cyclohexane (approximately 5 times volume of reaction mixture), and the precipitated solid collected by filtration and dried in a 30° C. vacuum oven. The dried white solid was designated Example 3 and identified as the polymer of NIPAAM/VDMA with a plurality of the dimethyl azlactone monomeric units derivatized with HEMA to provide monomeric units of the following structure (Me=CH$_3$):

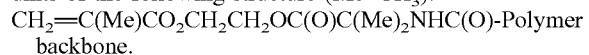
backbone.

Example 4

Derivatization of Polymer F: [MPA-(NIPAAM (71.5)/HEMA(28.5))] with VDMA (MPA=HO$_2$CCH$_2$CH$_2$CH$_2$S)

Polymer F (2.5 parts) was dissolved in THF (5 parts) in a reaction vessel to form a clear solution to which was added DBU (0.04 parts) and then VDMA (0.44 parts). The vessel was sealed and maintained at 40° C. for 1 hour. The resulting polymer solution was poured into a large excess of cyclohexane (approximately 5 times volume of reaction mixture) and the precipitated solid collected by filtration and dried in a 30° C. vacuum oven. The dried solid was designated Example 4 and identified as the Polymer of MPA-(NIPAAM/HEMA) with a plurality of the HEMA monomeric units and the MPA moiety derivatized with VDMA.

Example 5

Derivatization of Polymer G:

[MPA-(NIPAAM (76.9)/HEMA (15.5)/AAM (7.6))] with VDMA

Polymer G (5 parts) was dissolved in THF (10 parts) in a reaction vessel to form a clear solution to which was added DBU (0.04 parts) and then VDMA (0.44 parts). The resulting reaction mixture was stirred and heated at 40° C. for 1 hour. The resulting polymer solution was poured into a large excess of cyclohexane (approximately 5 times volume of reaction mixture) and the precipitated solid collected by filtration and dried in a 30° C. vacuum oven. The dried solid was designated Example 5 and identified as the Polymer of MPA-(NIPAAM/HEMA/AAM) with a plurality of the HEMA monomeric units and the MPA moiety derivatized with VDMA.

Example 6

Thermal Polymerization (Cross-Linking) of Examples 4 and 5

In two separate vials, the polymers of Examples 4 and 5 (10 parts in each vial) were combined with water (30 parts) and V-50 (0.01 parts) and the resulting mixtures purged with nitrogen for 1 minute. The vials were sealed and heated in a hot-water bath for 10 minutes. A solid lump of material separated out in both vials. The solids were isolated by filtration, dried and found in both cases to be insoluble in water.

Example 7

Evaluation of Polymer Thermoreversibility Properties

Examples 1–3 in individual vials (5 parts each) were combined with chilled (5° C.) water (20 parts) and thoroughly mixed at 5° C. until either a clear solution or a homogeneous dispersion was obtained. The resulting compositions were designated Samples 7a, 7b, and 7c, respectively.

Two-gram aliquots of Samples 7a, 7b, and 7c were transferred to 2-dram glass vials and sealed with a screw cap. The Samples were examined visually at 5° C. and 22° C. for fluidity and homogeneity by observing whether the compositions readily flowed upon inversion of the vial. The vials were then heated to 37° C. in a water bath for 1 minute and the compositions again observed for fluidity and or phase separation. Observation results are reported in Table 1.

TABLE 1

| Composition | 5° C. | 22° C. | 37° C. |
| --- | --- | --- | --- |
| Example 1 (Sample 7a) p(NIPAAM/AAM/VDMA)~HEMA | White Dispersion | White Dispersion | Precipitated Particles |
| Example 2 (Sample 7b) p(NIPAAM/HEMA)~IEM | White Dispersion | White Dispersion | Gellation (Solid Gel) |
| Example 3 (Sample 7c) p(NIPAAM/VDMA)~HEMA | Clear Solution | Clear Solution | Precipitated Particles (Phase Separation) |

All samples were flowable compositions at 5° C. and 22° C. and all produced either a solid cohesive gel or precipitation of substantial amounts of solid particulates upon heating to 37° C. In each case, cooling the compositions back to 5° C. or 22° C. resulted in the regeneration of a fluid flowable solution. These compositions were therefore found to exhibit thermoreversible behavior.

Example 8

Photopolymerization (Cross-Linking) of Example 2

To Example 2 (0.40 parts) dispersed in 1.60 parts of 5° C. water in a 2-dram vial was added the ternary initiator system comprised of CPQ (0.01 parts), EDMAB (0.01 parts), and DPIHFP (0.01 parts) and the resulting dispersion mixed thoroughly. This composition was designated Sample 8a and, like Sample 7b above, was a fluid and flowable white dispersion at 5° C. and 22° C. and a cohesive solid gel when heated for 30 seconds at 37° C. The composition could be reversibly converted to a liquid dispersion or to a cohesive solid gel upon cooling or heating, respectively.

Sample 8a in gel form at 37° C. in a glass vial was irradiated for 60 seconds with a FX 3000 dental curing light (3M ESPE, St. Paul, Minn.) by placing the tip of the light guide in direct contact with the vial and rotating the vial throughout the duration of the light exposure. The gelled sample was then cooled to 50° C. for 5 minutes and observed to be a rubbery solid. The sample was no longer thermoreversible and the experiment demonstrated that an irreversible cross-linked hydrogel could be obtained by photopolymerization.

An identical Sample 8a in fluid form at 22° C. was irradiated in the same manner. Following irradiation, the sample remained as a fluid flowable dispersion at 5° C. and 22° C.

Example 9

Photopolymerization (Cross-Linking) of Example 2+PEGDMA 400

To Example 2 (0.36 parts) dispersed in water (1.44 parts) in a 2-dram glass vial was added PEGDMA 400 (0.20 parts) and the ternary initiator system comprised of CPQ (0.01 parts), EDMAB (0.01 parts), and DPIHFP (0.01 parts) and the resulting dispersion mixed thoroughly. This composition was designated Sample 9a and, like Samples 7b and 8a above, was a white dispersion that readily flowed upon inversion of the vial at 5° C. and 22° C. However, when heated for 60 seconds at 37° C., substantial phase separation was observed in the form of a clear liquid component and a white cohesive gel. Subsequent cooling of the phase separated composition to 5° C. or 22° C. resulted in the regeneration of a fluid flowable dispersion and thus the composition demonstrated thermoreversible behavior.

Sample 9a was irradiated at 37° C. in a glass vial by the procedure described in Example 8. Another vial of Sample 9a was irradiated in the same manner at 22° C. Following irradiation at both temperatures, the compositions transformed into rubbery solids that did not exhibit a significant change in appearance when cooled or heated between 5° C. and 22° C. The compositions remained as rubbery solids and did not exhibit thermoreversible behavior.

Example 10

Preparation of Poly(AA(40)/ITA(20)/NIPAAM(20)/TMA-BF$_4$(20)) in THF

AA (40 parts), ITA (20 parts), NIPAAM (20 parts), TMA-BF$_4$ (20 parts), VAZO-67 (1.0 part), and THF (300 parts) were combined in a reaction vessel and the resulting mixture purged with nitrogen for 2 minutes. The vessel was sealed and maintained at 65° C. in a constant temperature rotating device for 18 hours during which time a white solid precipitate formed. After cooling to room temperature, water (300 parts) was added to the mixture with agitation until the solid was dissolved. The resulting polymer solution was designated Example 10 and identified as the polymer of AA (40), ITA (20), NIPAAM (20), and TMA-BF$_4$ (20) with weight ratios indicated in parentheses. The polymer solution was determined to have 18.4% solids.

Examples 11–17

Preparation of NIPAAM-Containing Polymers in THF

Polymer solutions designated Examples 11–17 were prepared as described for Example 10 and are listed as follows with monomeric units, weight ratios, and % Solids indicated:

Example 11: AA(40)/ITA(20)/NIPAAM(20)/TMA-BF$_4$(18)/LA(2); 21.7% Solids
Example 12: AA(40)/ITA(20)/NIPAAM(20)/TMA-BF$_4$(18)/SiMac(2); 19.2% Solids
Example 13: AA(40)/ITA(20)/NIPAAM(20)/TMA-BF$_4$(18)/ODA(2); 18.8% Solids
Example 14: AA(40)/ITA(20)/NIPAAM(20)/TMA-BF$_4$(19)/SiMac(1); 25.7% Solids
Example 15*: AA(40)/ITA(17)NIPAAM(20)/TMA-BF$_4$(18)/ODA(2)/A-174(3); 20.0% Solids
Example 16: AA(40)/ITA(20)/MeFBSEA(1)/NIPAAM(20)/TMA-BF$_4$(19); 15.3% Solids
Example 17: AA(40)/ITA(20)/MeFBSEA(1)/NIPAAM(20)/TMA-BF$_4$(19); 13.3% Solids

*Example 15 polymer solution was made in a 1:1 THF-Ethanol solvent and no water was added after polymerization.

Example 18

Preparation of Poly(AA(40)/ITA(20)/NIPAAM(20)/TMA-BF$_4$(18)/SiMac(2)) in Water

AA (40 parts), ITA (20 parts), NIPAAM (20 parts), TMA-BF$_4$ (18 parts), SiMac (2 parts), V-50 (1 part), and DI water (300 parts) were combined in a reaction vessel and the resulting mixture purged with nitrogen for 5 minutes. The vessel was sealed and maintained at 60° C. in a constant temperature rotating device for 30 hours. Upon cooling to room temperature a viscous polymer solution was obtained that was designated Example 9 and identified as the polymer of AA (40), ITA (20), NIPAAM (20), TMA-BF$_4$(18), and SiMac (2 parts) with weight ratios indicated in parentheses. The polymer solution was determined to have 20.0% solids.

Examples 19–21

Preparation of NIPAAM-Containing Polymers in Water

Polymer solutions designated Examples 19–21 were prepared as described for Example 18 and are listed as follows with monomeric units, weight ratios, and % Solids indicated:

Example 19: AA(40)/ITA(20)/NIPAAM(20)/TMA-BF$_4$(14)/DMA-C$_{16}$Br(4)/SiMac(2); 19.7% Solids
Example 20: AA(10)/ITA(10)/NIPAAM(60)/TMA-BF$_4$(20); 15.2% Solids
Example 21: AA(20)/ITA(20)/NIPAAM(20)/NVP(20)/TMA-BF$_4$(20); 17.0% Solids

Examples 22–24

Polymers Derivatized with IEM

AA (40 parts), ITA (20 parts), NIPAAM (20 parts), TMA-BF$_4$ (18 parts), ODA (2 parts), VAZO-65 (1 part), and THF (300 parts) were combined in a reaction vessel and the resulting mixture purged with nitrogen for 2 minutes. The vessel was sealed and maintained at 65° C. in a constant temperature rotating device for 18 hours during which time a white solid precipitate formed. After cooling to room temperature, DMF (30 parts) was added to the mixture to dissolve the solid and to the resulting solution was added IEM (1.1 parts), DBTDL (0.04 parts), and BHT (0.001 parts). After heating at 40° C. for 1 hour, the resulting polymer solution was poured into a large excess of ethyl acetate and the precipitated solid collected by filtration. The solid was washed two times with ethyl acetate, dried, and dissolved in DI water to make a 22.5% solids solution that was designated Example 22 and identified as the polymer of AA (40), ITA (20), NIPAAM (20), TMA-BF$_4$ (18), and ODA (2) with weight ratios indicated in parentheses and with a plurality (approximately ten mole percent) of the carboxy acid units derivatized with IEM to provide monomeric units of the following structure (Me=CH$_3$):
CH$_2$=C(Me)CO$_2$CH$_2$CH$_2$NHC(O)-Polymer backbone.

Examples 23 and 24 were prepared in a similar manner and are listed below.

Example 23: AA(40)/ITA(20)/NIPAAM(20)/MeFBSEMA(1)TMA-BF$_4$(19)/~IEM; 2.8% Solids Example 24: AA(40)/ITA(20)/NIPAAM(20)/MeFBSEMA(5)TMA-BF$_4$(15)/~IEM; 21.8% Solids Examples 25–32

Preparation of Poly(NIPAAM(55)/AA(20)/IBMA(20)/LA(5)) in Isopropanol

NIPAAM (55 parts), AA (20 parts), IBMA (20 parts), LA (5 parts), VAZO-67 (1.0 part), and isopropanol (200 parts) were combined in a reaction vessel and the resulting mixture purged with nitrogen for 2 minutes. The vessel was sealed and maintained at 65° C. in a constant temperature rotating device for 18 hours during which time a clear viscous polymer solution formed. A second charge of VAZO-67 (0.20 parts) was added to the reaction vessel and the solution heated at 65° C. for an additional 8 hours. After cooling to room temperature, the resulting polymer solution was poured into a large excess of ethyl acetate and the precipitated solid polymer collected by filtration. The solid was washed two times with ethyl acetate and dried in a vacuum oven at 40° C. The dried solid was designated Example 25 and identified as the polymer of NIPAAM (55), AA (20), IBMA (20), and LA (5) with weight ratios indicated in parentheses.

Dried polymers designated Examples 26–32 were prepared as described for Example 25 and are listed as follows with monomeric units and weight ratios indicated:

Example 26: NIPAAM(45), AA(20), ITA(10), IBMA(20), LA(5)
Example 27: NIPAAM(45), AA(30), IBMA(20), SiMac(5)
Example 28: NIPAAM(35), AA(30), ITA(10), IBMA(25)
Example 29: NIPAAM(55), AA(20), IBMA(20), SiMac(5)
Example 30: NIPAAM(20), AA(50), IBMA(25), SiMac(5)
Example 31: NIPAAM(60), AA(20), IBMA(20)
Example 32: NIPAAM(55), AA(20), IBMA(20), LA(5)

EVALUATIONS

Evaluation of Polymer Retention Times on Tooth Surfaces

To the polymer solutions designated Examples 11–14 and 29 was added 0.014% by weight of a red pigment (D&C Red 30 Talc Lake Sensient code: K7094, Sensient Technologies, St. Louis, Mo.) to provide Samples A–D listed in Table 2. Similarly, the red pigment was added to the product available under the trade designation SIMPLY WHITE (Colgate, New York, N.Y.) to provide Control Sample A (CR-A). These Samples were then evaluated for retention on teeth by using the following procedure.

Five extracted bovine teeth were removed from their storage container filled with water, and briefly patted with a paper towel. Samples A–D and CR-A were then individually brushed on each tooth and after 1 minute, the coated teeth were immersed in a water bath that was maintained at 37° C. and continuously agitated. The teeth were visually monitored over 1 hour for changes in the intensity and continuity of the red color on the tooth. The period of time that the red-colored polymer coating remained on a tooth was reported as the "Retention Time". After 1 hour, the coated teeth were removed from the water bath and probed gently to gauge the integrity of the tooth coatings. Results are provided in Table 2. Overall, based on direct observations of color intensity and continuity, Samples A–D all appeared to maintain a retentive film for greater than 1 hour, whereas Sample CR-A lost substantially all of the red coating color within 5 minutes.

TABLE 2

| Sample | Composition | Retention Time | Observations |
|--------|-------------|----------------|--------------|
| A | Ex. 11 + red pigment | >1 hour | Coating was retained but fragile to the touch (loss of red color and coating fragmented when probed) |
| B | Ex. 12 + red pigment | >1 hour | Coating less fragile then Samples B and D (more difficult to remove red color and coating with probe) |
| C | Ex. 13 + red pigment | >1 hour | Coating was retained but fragile to the touch (loss of red color and coating fragmented when probed) |
| D | Ex. 14 + red pigment | >1 hour | Least fragile coating (most difficult coating to remove red color and fragment coating with probe) |
| E | Ex. 29 | >1 hour | Coating was retained |
| CR-A | "SIMPLY WHITE" + red pigment | <5 minutes | Color loss began immediately when coated tooth placed in water bath. |

Evaluation of Polymers/Whitening Agent on Tooth Surfaces

To the polymer solutions designated Examples 11–14 was added 18% by carbamide peroxide (Sigma-Aldrich) to provide Samples E–H listed in Table 3. These Samples were then evaluated for whitening of teeth by using the following procedure.

Eight extracted bovine teeth were removed from their storage container filled with water and stained by soaking in a solution of Classic Coke and coffee for 24 hours at 38° C. An initial determination of tooth shade was determined for each tooth by comparing the shade with a VITA Shade Guide (Vident, Brea, Calif.). Samples E–H were then individually painted on the surface of each tooth with a brush and air dried for 30 seconds. Two teeth were identically coated with each polymer solution sample. The coated teeth were immersed in a water bath that was maintained at 37° C. and continuously agitated. After 30–45 minutes, the coated teeth were removed from the water bath and coated again with the samples in a similar manner. This procedure was repeated until the teeth had been coated a total of 10 times. The teeth were then removed from the water bath and a final determination of tooth shade was determined for each tooth by comparing the shade with the VITA Shade Guide. The differences between the initial and the final stain values were calculated with a larger difference being indicative of increased tooth whitening. Results as an average of the two replicates per sample are provided in Table 3. All samples showed an increase in teeth whitening when evaluated under the conditions of this test method.

TABLE 3

| Sample | Composition | Change in Stain Value (Increase in Whitening) |
|---|---|---|
| E | Ex. 11 + carbamide peroxide | 3.5 |
| F | Ex. 12 + carbamide peroxide | 2.5 |
| G | Ex. 13 + carbamide peroxide | 4.0 |
| H | Ex. 14 + carbamide peroxide | 3.5 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A reactive polymer prepared by a method comprising:
combining and copolymerizing monomers comprising N-isopropylacrylamide and a hydroxy-functional (meth)acrylate monomer to form a hydroxy-functional polymer; and
reacting the hydroxy-functional polymer with a hydroxy-reactive material selected from the group consisting of a (meth)acrylate-functional isocyanate, a (meth)acrylate-functional epoxide, a vinyl azlactone, and combinations thereof,
wherein the reactive polymer comprises a non-terminal monomeric unit comprising a pendant ethylenically unsaturated group and copolymerized N-isopropylacrylamide.

2. The reactive polymer of claim 1 wherein the pendant ethylenically unsaturated group comprises a (meth)acrylate group.

3. A reactive polymer prepared by a method comprising:
combining and copolymerizing monomers comprising N-isopropylacrylamide and a hydroxy-functional (meth)acrylate monomer to form a hydroxy-functional polymer; and
reacting the hydroxy-functional polymer with a hydroxy-reactive material selected from the group consisting of a (meth)acrylate-functional isocyanate, a (meth)acrylate-functional epoxide, a vinyl azlactone, and combinations thereof,
wherein the reactive polymer comprises:
1% by weight to 90% by weight of non-terminal monomeric units comprising a pendant ethylenically unsaturated group, based on the total weight of monomeric units; and
1% by weight to 99% by weight of copolymerized N-isopropylacrylamide, based on the total weight of monomeric units.

4. The reactive polymer of claim 3 comprising:
5% by weight to 50% by weight of non-terminal monomeric units comprising a pendant ethylenically unsaturated group, based on the total weight of monomeric units; and
50% by weight to 95% by weight of copolymerized N-isopropylacrylamide, based on the total weight of monomeric units.

5. The reactive polymer of claim 4 comprising:
10% by weight to 30% by weight of non-terminal monomeric units comprising a pendant ethylenically unsaturated group, based on the total weight of monomeric units; and
70% by weight to 90% by weight of copolymerized N-isopropylacrylamide, based on the total weight of monomeric units.

6. A reactive polymer prepared by a method comprising:
combining and copolymerizing monomers comprising N-isopropylacrylamide and a hydroxy-functional (meth)acrylate monomer to form a hydroxy-functional polymer; and
reacting the hydroxy-functional polymer with a hydroxy-reactive material selected from the group consisting of a (meth)acrylate-functional isocyanate, a (meth)acrylate-functional epoxide, a vinyl azlactone, and combinations thereof,
wherein the reactive polymer comprises a polymeric backbone having at least three ethylenically unsaturated pendant groups and a plurality of pendant groups of the formula —C(O)NHCH(CH$_3$)$_2$ attached to the backbone.

7. The reactive polymer of claim 6 wherein the ethylenically unsaturated pendant groups comprise (meth)acrylate groups.

8. A composition comprising:
a reactive polymer according to claim 1; and
water.

9. The composition of claim 8 wherein the composition is thermally responsive.

10. The composition of claim 8 wherein the composition is suitable for use in the oral environment.

11. The composition of claim 8 wherein the pendant ethylenically unsaturated group comprises a (meth)acrylate group.

12. The composition of claim 8 further comprising an initiator.

13. The composition of claim 12 wherein the initiator is a photoinitiator.

14. The composition of claim 12 wherein the initiator is a free radical inititator.

15. The composition of claim 8 further comprising an oxidizing agent and a reducing agent.

16. The composition of claim 8 further comprising a polymerizable component different than the reactive polymer.

17. A composition comprising:
1% by weight to 99% by weight of a reactive polymer according to claim 3, based on the total weight of the composition; and
water.

18. A reactive polymer prepared by a method comprising:
combining and copolymerizing monomers comprising N-isopropylacrylamide and vinyl azlactone to form an azlactone-functional polymer; and
reacting the azlactone-functional polymer with a hydroxy-functional (meth)acrylate,
wherein the reactive polymer comprises a non-terminal monomeric unit comprising a pendant ethylenically unsaturated group and copolymerized N-isopropylacrylamide.

19. The reactive polymer of claim 18 wherein the pendant ethylenically unsaturated group comprises a (meth)acrylate group.

20. A reactive polymer prepared by a method comprising:
combining and copolymerizing monomers comprising N-isopropylacrylamide and vinyl azlactone to form an azlactone-functional polymer; and
reacting the azlactone-functional polymer wit a hydroxy-functional (meth)acrylate wherein the reactive polymer comprises:
1% by weight to 90% by weight of non-terminal monomeric units comprising a pendant ethylenically unsaturated group, based on the total weight of monomeric units; and
1% by weight to 99% by weight of copolymerized N-isopropylacrylamide, based on the total weight of monomeric units.

21. The reactive polymer of claim 20 comprising:
5% by weight to 50% by weight of non-terminal monomeric units comprising a pendant ethylenically unsaturated group, based on the total weight of monomeric units; and
50% by weight to 95% by weight of copolymerized N-isopropylacrylamide, based on the total weight of monomeric units.

22. The reactive polymer of claim 21 comprising:
10% by weight to 30% by weight of non-terminal monomeric units comprising a pendant ethylenically unsaturated group, based on the total weight of monomeric units; and
70% by weight to 90% by weight of copolymerized N-isopropylacrylamide, based on the total weight of monomeric units.

23. A reactive polymer prepared by a method comprising:
combining and copolymerizing monomers comprising N-isopropylacrylamide and vinyl azlactone to form an azlactone-functional polymer; and
reacting the azlactone-functional polymer with a hydroxy-functional (meth)acrylate,
wherein the reactive polymer comprises a polymeric backbone having at least three ethylenically unsaturated pendant groups and a plurality of pendant groups of the formula $-C(O)NHCH(CH_3)_2$ attached to the backbone.

24. The reactive polymer of claim 23 wherein the ethylenically unsaturated pendant groups comprise (meth)acrylate groups.

25. A composition comprising:
a reactive polymer according to claim 18; and
water.

26. The composition of claim 25 wherein the composition is thermally responsive.

27. The composition of claim 25 wherein the composition is suitable for use in the oral environment.

28. The composition of claim 25 wherein the pendant ethylenically unsaturated group comprises a (meth)acrylate group.

29. The composition of claim 25 further comprising an initiator.

30. The composition of claim 29 wherein the initiator is a photoinitiator.

31. The composition of claim 29 wherein the initiator is a free radical inititator.

32. The composition of claim 25 further comprising an oxidizing agent and a reducing agent.

33. The composition of claim 25 further comprising a polymerizable component different than the reactive polymer.

34. A composition comprising:
1% by weight to 99% by weight of a reactive polymer according to claim 20, based on the total weight of the composition; and
water.

* * * * *

UNITED STATES PATENT AND TRADEMARK OFFICE
CERTIFICATE OF CORRECTION

PATENT NO. : 7,223,826 B2
APPLICATION NO. : 10/626341
DATED : May 29, 2007
INVENTOR(S) : Mahfuza B. Ali It is certified that error appears in the above-identified patent and that said Letters Patent is hereby corrected as shown below:

On Page 2, in Column 2, under (Other Publications)
Line 1, delete "Polysilxoane" and insert -- Polysiloxane --, therefor.
Line 4, delete "Makromal." and insert -- Makromol. --, therefor.
Line 13, delete "N-Isoproplacrylamide," and insert -- N-Isopropylacrylamide, -- therefor.
Line 22, delete "Dentrifrice," and insert -- Dentifrice, --, therefor.
Line 28, delete "Science" and insert -- Science, --, therefor.

Column 7
Line 11, delete "isocyante" and insert -- isocyanate --, therefor.

Column 16
Line 23, delete "THY" and insert -- THF --, therefor.

Column 18
Line 63, delete "50°C." and insert -- 5°C. --, therefor.

Column 20
Line 3, delete "(17)NIPAAM" and insert -- (17)/NIPAAM --, therefor.

Column 24
Line 46, in Claim 14, delete "inititator." and insert -- initiator. --, therefor.

Column 25
Line 8, in Claim 20, delete "wit" and insert -- with --, therefor.

UNITED STATES PATENT AND TRADEMARK OFFICE
CERTIFICATE OF CORRECTION

PATENT NO. : 7,223,826 B2
APPLICATION NO. : 10/626341
DATED : May 29, 2007
INVENTOR(S) : Mahfuza B. Ali It is certified that error appears in the above-identified patent and that said Letters Patent is hereby corrected as shown below:

<u>Column 26</u>
Line 25, in Claim 31, delete "inititator." and insert -- initiator. --, therefor.

Signed and Sealed this

Thirteenth Day of May, 2008

JON W. DUDAS
*Director of the United States Patent and Trademark Office*